United States Patent
Cropper et al.

(10) Patent No.: US 8,361,109 B2
(45) Date of Patent: Jan. 29, 2013

(54) MULTI-PLANAR OBTURATOR WITH FOLDABLE RETRACTOR

(75) Inventors: Michael S. Cropper, Edgewood, KY (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 792 days.

(21) Appl. No.: 12/478,882

(22) Filed: Jun. 5, 2009

(65) Prior Publication Data

US 2010/0312062 A1 Dec. 9, 2010

(51) Int. Cl.
*A61B 17/15* (2006.01)

(52) U.S. Cl. ...................................... 606/210

(58) Field of Classification Search .......... 600/200–210, 600/215, 184; 604/164.02, 164.03, 137.07, 604/104, 256, 264, 272, 103.06, 103.14, 604/106, 107, 239; 606/198, 190, 191; 623/1.1
See application file for complete search history.

(56) References Cited

U.S. PATENT DOCUMENTS

| | | |
|---|---|---|
| 2,129,391 A | 9/1938 | Wappler |
| 3,402,710 A | 9/1968 | Paleschuck |
| 3,654,965 A | 4/1972 | Gramain |
| 4,112,932 A | 9/1978 | Chiulli |
| 4,306,545 A | 12/1981 | Ivan et al. |
| 4,379,458 A | 4/1983 | Bauer et al. |
| 4,402,683 A | 9/1983 | Kopman |
| 4,417,888 A | 11/1983 | Cosentino et al. |
| 5,010,925 A | 4/1991 | Atkinson et al. |
| 5,091,435 A | 2/1992 | Suzuki et al. |
| 5,183,471 A | 2/1993 | Wilk |
| 5,197,955 A | 3/1993 | Stephens et al. |
| 5,207,213 A | 5/1993 | Auhll et al. |
| 5,209,737 A | 5/1993 | Ritchart et al. |
| 5,209,741 A | 5/1993 | Spaeth |
| 5,235,966 A | 8/1993 | Jamner |

(Continued)

FOREIGN PATENT DOCUMENTS

| | | |
|---|---|---|
| DE | 19814576 A1 | 10/1999 |
| DE | 20022005 | 4/2001 |

(Continued)

OTHER PUBLICATIONS

International Search Report and Written Opinion for International App. No. PCT/US2010/036811 dated Sep. 14, 2010 (6 pages).

(Continued)

*Primary Examiner* — Heidi M Eide
(74) *Attorney, Agent, or Firm* — Nutter McClennen & Fish LLP

(57) ABSTRACT

Various methods and devices are provided for providing surgical access to a body cavity using a surgical access device that can include an elongate flexible member having proximal and distal ends and a sidewall extending therebetween. The elongate flexible member can be movable between a first position in which the elongate flexible member has at least one longitudinal fold formed in the sidewall such that a width of a longitudinal opening extending through the elongate flexible member is reduced, and a second position in which the fold in the sidewall is unfolded such that a width of the longitudinal opening is increased. In some embodiments, an obturator having expansion members can be used to unfold the elongate flexible member.

19 Claims, 12 Drawing Sheets

U.S. PATENT DOCUMENTS

| | | |
|---|---|---|
| 5,269,772 A | 12/1993 | Wilk |
| 5,308,336 A | 5/1994 | Hart et al. |
| 5,312,417 A | 5/1994 | Wilk |
| 5,320,611 A | 6/1994 | Bonutti et al. |
| 5,342,315 A | 8/1994 | Rowe et al. |
| 5,353,784 A * | 10/1994 | Nady-Mohamed ........... 600/205 |
| 5,366,478 A | 11/1994 | Brinkerhoff et al. |
| 5,385,553 A | 1/1995 | Hart et al. |
| 5,385,560 A | 1/1995 | Wulf |
| 5,391,154 A | 2/1995 | Young |
| 5,431,676 A | 7/1995 | Dubrul et al. |
| 5,443,452 A | 8/1995 | Hart et al. |
| 5,443,484 A | 8/1995 | Kirsch et al. |
| 5,476,475 A | 12/1995 | Gadberry |
| 5,480,410 A | 1/1996 | Cuschieri et al. |
| 5,531,758 A | 7/1996 | Uschold et al. |
| 5,545,179 A | 8/1996 | Williamson, IV |
| 5,562,677 A | 10/1996 | Hildwein et al. |
| 5,569,205 A | 10/1996 | Hart et al. |
| 5,569,254 A | 10/1996 | Carlson et al. |
| 5,584,850 A | 12/1996 | Hart et al. |
| 5,628,732 A | 5/1997 | Antoon, Jr. et al. |
| 5,634,911 A | 6/1997 | Hermann et al. |
| 5,634,937 A | 6/1997 | Mollenauer et al. |
| 5,643,301 A | 7/1997 | Mollenauer |
| 5,653,705 A | 8/1997 | de la Torre et al. |
| 5,653,718 A | 8/1997 | Yoon |
| 5,672,168 A | 9/1997 | de la Torre et al. |
| 5,676,657 A | 10/1997 | Yoon |
| 5,695,448 A | 12/1997 | Kimura et al. |
| 5,707,359 A | 1/1998 | Bufalini |
| 5,752,970 A | 5/1998 | Yoon |
| 5,782,812 A | 7/1998 | Hart et al. |
| 5,797,888 A | 8/1998 | Yoon |
| 5,803,919 A | 9/1998 | Hart et al. |
| 5,814,058 A | 9/1998 | Carlson et al. |
| 5,827,319 A | 10/1998 | Carlson et al. |
| 5,843,040 A | 12/1998 | Exline |
| 5,865,807 A | 2/1999 | Blake, III |
| 5,868,762 A | 2/1999 | Cragg et al. |
| 5,882,344 A | 3/1999 | Stouder, Jr. |
| 5,891,013 A | 4/1999 | Thompson |
| 5,899,208 A | 5/1999 | Bonadio |
| 5,906,577 A | 5/1999 | Beane et al. |
| 5,946,280 A | 8/1999 | Ohkubo |
| 5,957,913 A | 9/1999 | de la Torre et al. |
| 5,990,382 A | 11/1999 | Fox |
| 5,997,515 A | 12/1999 | de la Torre et al. |
| 6,024,736 A | 2/2000 | de la Torre et al. |
| RE36,702 E | 5/2000 | Green et al. |
| 6,056,766 A | 5/2000 | Thompson et al. |
| 6,066,090 A | 5/2000 | Yoon |
| 6,077,288 A | 6/2000 | Shimomura et al. |
| 6,080,174 A | 6/2000 | Dubrul et al. |
| 6,086,603 A | 7/2000 | Termin et al. |
| 6,120,513 A | 9/2000 | Bailey et al. |
| 6,123,689 A | 9/2000 | To et al. |
| 6,142,396 A | 11/2000 | Gallus |
| 6,142,936 A | 11/2000 | Beane et al. |
| 6,162,196 A | 12/2000 | Hart et al. |
| 6,217,555 B1 | 4/2001 | Hart et al. |
| 6,245,052 B1 | 6/2001 | Orth et al. |
| 6,258,069 B1 | 7/2001 | Carpentier et al. |
| 6,277,064 B1 | 8/2001 | Yoon |
| 6,315,770 B1 | 11/2001 | de la Torre et al. |
| 6,319,246 B1 | 11/2001 | de la Torre et al. |
| 6,325,812 B1 | 12/2001 | Dubrul et al. |
| 6,348,034 B1 | 2/2002 | Thompson |
| 6,352,503 B1 | 3/2002 | Matsui et al. |
| 6,440,061 B1 | 8/2002 | Wenner et al. |
| 6,440,063 B1 | 8/2002 | Beane et al. |
| 6,447,489 B1 | 9/2002 | Peterson |
| 6,454,783 B1 | 9/2002 | Piskun |
| 6,458,077 B1 | 10/2002 | Boebel et al. |
| 6,488,620 B1 | 12/2002 | Segermark et al. |
| 6,551,270 B1 | 4/2003 | Bimbo et al. |
| 6,551,282 B1 | 4/2003 | Exline et al. |
| 6,589,167 B1 | 7/2003 | Shimomura et al. |
| 6,605,063 B2 | 8/2003 | Bousquet |
| 6,669,674 B1 | 12/2003 | Macoviak et al. |
| 6,702,787 B2 | 3/2004 | Racenet et al. |
| 6,706,033 B1 | 3/2004 | Martinez et al. |
| 6,706,050 B1 | 3/2004 | Giannadakis |
| 6,849,064 B2 * | 2/2005 | Hamada ................... 604/164.01 |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,972,026 B1 | 12/2005 | Caldwell et al. |
| 7,014,628 B2 | 3/2006 | Bousquet |
| 7,052,454 B2 * | 5/2006 | Taylor .......................... 600/114 |
| 7,083,626 B2 | 8/2006 | Hart et al. |
| 7,118,528 B1 | 10/2006 | Piskun |
| 7,163,510 B2 * | 1/2007 | Kahle et al. ................... 600/208 |
| 7,163,525 B2 | 1/2007 | Franer |
| 7,214,185 B1 | 5/2007 | Rosney et al. |
| 7,229,408 B2 | 6/2007 | Douglas et al. |
| 7,338,473 B2 | 3/2008 | Campbell et al. |
| 7,344,547 B2 | 3/2008 | Piskun |
| 7,371,227 B2 | 5/2008 | Zeiner |
| 7,393,322 B2 | 7/2008 | Wenchell |
| 7,449,011 B2 | 11/2008 | Wenchell et al. |
| 7,481,795 B2 | 1/2009 | Thompson et al. |
| 2002/0156432 A1 | 10/2002 | Racenet et al. |
| 2003/0028179 A1 | 2/2003 | Piskun |
| 2003/0139756 A1 | 7/2003 | Brustad |
| 2003/0216770 A1 | 11/2003 | Persidsky et al. |
| 2004/0015185 A1 | 1/2004 | Ewers et al. |
| 2004/0019322 A1 | 1/2004 | Hoffmann |
| 2004/0082969 A1 | 4/2004 | Kerr |
| 2004/0106942 A1 | 6/2004 | Taylor et al. |
| 2004/0117032 A1 | 6/2004 | Roth |
| 2004/0138528 A1 | 7/2004 | Richter et al. |
| 2004/0199121 A1 | 10/2004 | Wenchell et al. |
| 2004/0215063 A1 | 10/2004 | Bonadio et al. |
| 2004/0230160 A1 | 11/2004 | Blanco |
| 2004/0230161 A1 | 11/2004 | Zeiner |
| 2004/0254426 A1 | 12/2004 | Wenchell |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0215862 A1 | 9/2005 | Larson et al. |
| 2005/0216028 A1 | 9/2005 | Hart et al. |
| 2005/0222582 A1 | 10/2005 | Wenchell |
| 2005/0267419 A1 | 12/2005 | Smith |
| 2005/0273132 A1 | 12/2005 | Shluzas et al. |
| 2005/0277946 A1 | 12/2005 | Greenhalgh |
| 2006/0012965 A1 | 1/2006 | Beall et al. |
| 2006/0019592 A1 | 1/2006 | Kupferberg et al. |
| 2006/0019723 A1 | 1/2006 | Vorenkamp et al. |
| 2006/0020241 A1 | 1/2006 | Piskun et al. |
| 2006/0020281 A1 | 1/2006 | Smith |
| 2006/0021061 A1 | 1/2006 | Cerri et al. |
| 2006/0021891 A1 | 2/2006 | Franer et al. |
| 2006/0025813 A1 | 2/2006 | Shelton et al. |
| 2006/0030755 A1 | 2/2006 | Ewers et al. |
| 2006/0071432 A1 | 4/2006 | Staudner |
| 2006/0129165 A1 | 6/2006 | Edoga et al. |
| 2006/0212061 A1 | 9/2006 | Wenchell |
| 2006/0212062 A1 | 9/2006 | Farascioni |
| 2006/0217665 A1 | 9/2006 | Prosek |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0247498 A1 | 11/2006 | Bonadio et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |

| | | | | | | |
|---|---|---|---|---|---|---|
| 2006/0264706 A1 | 11/2006 | Piskun | | EP | 1219253 A1 | 7/2002 |
| 2006/0270911 A1 | 11/2006 | Voegele et al. | | EP | 1350476 | 10/2003 |
| 2007/0049966 A1 | 3/2007 | Bonadio et al. | | EP | 1702575 A2 | 9/2006 |
| 2007/0060939 A1 | 3/2007 | Lancial et al. | | EP | 1731105 A1 | 12/2006 |
| 2007/0073110 A1* | 3/2007 | Larson et al. ............ 600/210 | | EP | 1774918 A1 | 4/2007 |
| 2007/0085232 A1 | 4/2007 | Brustad et al. | | EP | 2119404 A1 | 11/2009 |
| 2007/0088202 A1 | 4/2007 | Albrecht et al. | | FR | 2710270 A1 | 3/1995 |
| 2007/0088204 A1 | 4/2007 | Albrecht et al. | | JP | 2006320750 | 11/2006 |
| 2007/0088258 A1 | 4/2007 | Wenchell et al. | | WO | 9407552 A1 | 4/1994 |
| 2007/0088277 A1 | 4/2007 | McGinley et al. | | WO | 9602297 A1 | 2/1996 |
| 2007/0118021 A1 | 5/2007 | Pokorney | | WO | 9608897 A1 | 3/1996 |
| 2007/0118175 A1 | 5/2007 | Butler et al. | | WO | 9636283 A1 | 11/1996 |
| 2007/0151566 A1 | 7/2007 | Kahle et al. | | WO | 9743958 A1 | 11/1997 |
| 2007/0185453 A1 | 8/2007 | Michael et al. | | WO | 0032263 A1 | 6/2000 |
| 2007/0208312 A1 | 9/2007 | Norton et al. | | WO | 0041759 A1 | 7/2000 |
| 2007/0255219 A1 | 11/2007 | Vaugh et al. | | WO | 0108563 A2 | 2/2001 |
| 2008/0009797 A1 | 1/2008 | Stellon et al. | | WO | 0217800 A2 | 3/2002 |
| 2008/0025519 A1 | 1/2008 | Yu et al. | | WO | 2004030515 A2 | 4/2004 |
| 2008/0027476 A1 | 1/2008 | Piskun | | WO | 2005000454 A1 | 1/2005 |
| 2008/0051739 A1 | 2/2008 | McFarlane | | WO | 2005002454 A1 | 1/2005 |
| 2008/0058728 A1 | 3/2008 | Soltz et al. | | WO | 2005087112 A1 | 9/2005 |
| 2008/0065021 A1 | 3/2008 | Jenkins et al. | | WO | 2005094432 A2 | 10/2005 |
| 2008/0086080 A1 | 4/2008 | Mastri et al. | | WO | 2005097019 A2 | 10/2005 |
| 2008/0119821 A1 | 5/2008 | Agnihotri et al. | | WO | 2005097234 A2 | 10/2005 |
| 2008/0132765 A1 | 6/2008 | Beckman et al. | | WO | 2006057982 A2 | 6/2006 |
| 2008/0234550 A1* | 9/2008 | Hawkes et al. ............ 600/204 | | WO | 2007008741 A1 | 1/2007 |
| 2008/0255519 A1 | 10/2008 | Piskun et al. | | WO | WO 2007008741 | 1/2007 |
| 2008/0281161 A1 | 11/2008 | Albrecht et al. | | WO | 2007119232 A2 | 10/2007 |
| 2009/0005799 A1 | 1/2009 | Franer et al. | | WO | 2008024502 A2 | 2/2008 |
| 2009/0082731 A1 | 3/2009 | Moreno | | WO | 2008028149 A2 | 3/2008 |
| 2009/0118587 A1 | 5/2009 | Voegele et al. | | WO | 2008121294 A1 | 10/2008 |
| 2009/0187079 A1 | 7/2009 | Albrecht et al. | | WO | 2009035663 A2 | 3/2009 |
| 2009/0270685 A1 | 10/2009 | Moreno et al. | | WO | WO 2009035663 | 3/2009 |
| 2009/0270686 A1 | 10/2009 | Duke et al. | | | | |
| 2009/0270818 A1 | 10/2009 | Duke | | | | |
| 2010/0010310 A1 | 1/2010 | Weisenburgh, II et al. | | | | |
| 2010/0081863 A1 | 4/2010 | Hess et al. | | | | |
| 2010/0081864 A1 | 4/2010 | Hess et al. | | | | |
| 2010/0081871 A1 | 4/2010 | Widenhouse et al. | | | | |
| 2010/0081880 A1 | 4/2010 | Widenhouse et al. | | | | |
| 2010/0081881 A1 | 4/2010 | Murray et al. | | | | |
| 2010/0081882 A1 | 4/2010 | Hess et al. | | | | |
| 2010/0081883 A1 | 4/2010 | Murray et al. | | | | |
| 2010/0081995 A1 | 4/2010 | Widenhouse et al. | | | | |
| 2010/0228090 A1 | 9/2010 | Weisenburgh, II et al. | | | | |
| 2010/0228091 A1 | 9/2010 | Widenhouse et al. | | | | |
| 2010/0228092 A1 | 9/2010 | Ortiz et al. | | | | |
| 2010/0228094 A1 | 9/2010 | Ortiz et al. | | | | |
| 2010/0228096 A1 | 9/2010 | Weisenburgh, II et al. | | | | |
| 2010/0228198 A1 | 9/2010 | Widenhouse et al. | | | | |
| 2010/0249525 A1 | 9/2010 | Shelton, IV et al. | | | | |
| 2010/0261970 A1 | 10/2010 | Shelton, IV et al. | | | | |
| 2010/0261972 A1 | 10/2010 | Widenhouse et al. | | | | |
| 2010/0261974 A1 | 10/2010 | Shelton, IV et al. | | | | |
| 2010/0262080 A1 | 10/2010 | Shelton, IV et al. | | | | |
| 2010/0268162 A1 | 10/2010 | Shelton, IV et al. | | | | |
| 2010/0274093 A1 | 10/2010 | Shelton, IV | | | | |
| 2010/0280327 A1 | 11/2010 | Nobis et al. | | | | |
| 2010/0312060 A1 | 12/2010 | Widenhouse et al. | | | | |
| 2010/0312061 A1 | 12/2010 | Hess et al. | | | | |
| 2010/0312062 A1 | 12/2010 | Cropper et al. | | | | |
| 2010/0312063 A1 | 12/2010 | Hess et al. | | | | |
| 2010/0312064 A1 | 12/2010 | Weisenburgh, II et al. | | | | |
| 2010/0312065 A1 | 12/2010 | Shelton, IV et al. | | | | |
| 2010/0312066 A1 | 12/2010 | Cropper et al. | | | | |
| 2010/0312189 A1 | 12/2010 | Shelton, IV et al. | | | | |

FOREIGN PATENT DOCUMENTS

| | | |
|---|---|---|
| DE | 20022005 U1 | 4/2001 |
| EP | 568383 A1 | 11/1993 |
| EP | 577400 A1 | 1/1994 |
| EP | 0637431 A1 | 2/1995 |
| EP | 646358 A1 | 4/1995 |
| EP | 709918 | 5/1996 |
| EP | 0776231 B1 | 6/1997 |
| EP | 950376 | 10/1999 |
| EP | 1219251 A1 | 7/2002 |
| EP | 1219252 A1 | 7/2002 |

OTHER PUBLICATIONS

International Search Report, from PCT/US10/36829, mailed Sep. 9, 2010 (5 pages).

European Search Report, EP 10250732, dated Jul. 28, 2010.

International Search Report and Written Opinion for Application No. PCT/US2010/037190, dated Sep. 22, 2010 (15 pages).

"Surgeon performs single-port laparoscopic surgery > Kidney removal with instructions inserted through single port access SPA > One Port Umbilicus Surgery OPUS > Uretero-pelvic junction repair > Bilateral pyeloplasty > Triport > Quadport > R-Port laparoscopic access device > Advanced Surgical Concepts ASC" Ideas for Surgery.com, Dec. 2007, 4 pages.

Desai, Mihir M. et al., "Laparoscopic and Robtic Urology-Scarless single port transumbilical nephrectomy and pyeloplasty: first clinical report," Journal Compilation, 2008 BJU International, 101, pp. 83-88.

Lee D, et al. Novel Approach to Minimizing Trocar Sites during Challenging Hand-Assisted Laparoscopic Surgery Utilizing the GelPort: Trans-Gel Instrument and Utilization, Journal of Endourology, vol. 17, No. 2, Mar. 2003, pp. 69-71.

Nakajima K, et al. Hand-assisted laparoscopic colorectal surgery using GelPort, Surg Endosc. Jan. 2004; 18(1)102-5. Epub Sep. 10, 2003.

Nakajima K, et al. Use of the surgical towel in colorectal hand-assisted laparoscopic surgery (HALS), Surg Endosc. Mar. 2004; 18(3):552-3.

Patel, R. et al. "Hand-Assisted Laparoscopic Devices: The Second Generation," Journal of Endourology, vol. 18, No. 7, Sep. 2004, pp. 649-653.

Rane, A. et al., "Single-Port Access Nephrectomy and Other Laparoscopic Urologic Procedures Using a Novel Laparoscopic Port (R-Port)," Urology, Aug. 2008; 72(2):260-264.

International Search Report and Written Opinion for Application No. PCT/US2010/036806, dated Sep. 3, 2010 (8 pages).

International Search Report and Written Opinion for Application No. PCT/US2010/036820, dated Oct. 22, 2010 (18 pages).

International Search Report, from PCT/US10/36829, mailed Sep. 9, 2010.

* cited by examiner

MULTI-PLANAR OBTURATOR WITH FOLDABLE RETRACTOR

FIELD OF THE INVENTION

The present invention relates to methods and devices for providing surgical access into a body cavity.

BACKGROUND OF THE INVENTION

Access ports are widely used in medical procedures to gain access to anatomical cavities ranging in size from the abdomen to small blood vessels, such as veins and arteries, epidural, pleural and subarachnoid spaces, heart ventricles, and spinal and synovial cavities. The use of access ports has become more common as they provide minimally invasive techniques for establishing a portal for a number of procedures, such as those involving the abdominal cavity. Reduced postoperative recovery time, markedly decreased post-operative pain and wound infection, and improved cosmetic outcome are well established benefits of minimally invasive surgery, derived mainly from the ability of surgeons to perform an operation utilizing smaller incisions of the body cavity wall.

In many surgical procedures, it is desirable to provide one or more working channels into a body cavity through which various instruments can be passed to view, engage, and/or treat tissue to achieve a diagnostic or therapeutic effect. In laparoscopic abdominal procedures for example, the abdominal cavity is generally insufflated with $CO_2$ gas to a pressure of around 15 mm Hg. The abdominal wall is pierced and one or more tubular cannulas, each defining a working channel, are inserted into the abdominal cavity. A laparoscopic telescope connected to an operating room monitor can be used to visualize the operative field and can be placed through one of the working channels. Other laparoscopic instruments such as graspers, dissectors, scissors, retractors, etc. can also be placed through one or more of the working channels to facilitate various manipulations by the surgeon and/or surgical assistant(s).

One problem with existing methods and devices is that existing surgical access devices that are configured to receive multiple instruments simultaneously have a very large size, and thus either require large incisions in tissue in order to place the surgical access device, or they cause damage to a smaller incision when the surgical access device is wedged into place. It can thus be difficult to position a large surgical access device in the incision, particularly in minimally invasive surgical procedures where the incision preferably relatively small.

Accordingly, there remains a need for methods and devices for positioning surgical access devices in tissue to form a pathway through the tissue and into a body cavity.

SUMMARY OF THE INVENTION

The present invention generally provides methods and devices for providing surgical access to an interior of a patient's body. In one embodiment, a surgical access device is provided that can include an obturator having an elongate shaft configured to create a pathway through tissue and into a body cavity and that can be radially expandable. The surgical access device can also include a flexible retractor having a longitudinal opening extending therethrough and configured to form a pathway through tissue for providing access to a body cavity. In one embodiment, the flexible retractor can include at least one longitudinal fold formed therein and configured such that insertion of the elongate shaft of the obturator into the opening and radial expansion of the elongate shaft unfolds the longitudinal fold to radially expand the longitudinal opening and thereby increase a size of a pathway formed through tissue when the flexible retractor is disposed within tissue. In some embodiments, the obturator can include an actuator effective to expand and retract the elongate shaft. The cross-sectional shape of the elongate shaft can generally have any shape as needed. In some embodiments, the cross-sectional shape can be substantially oblong in an expanded configuration.

The longitudinal fold can have many configurations. For example, the longitudinal fold can include first, second, third, and fourth longitudinal folds formed therein. In one embodiment, the first fold and the third fold can be opposed, and the second fold and the fourth fold can be opposed. The elongate shaft can be configured to expand in a first direction to unfold the first and third longitudinal folds. In addition, the elongate shaft can be configured to expand in a second direction to unfold the second and fourth longitudinal folds. The first and second directions can be offset by any amount, such as, for example, approximately 90 degrees. The longitudinal fold can optionally be biased to a folded state and/or to an expanded state.

In another exemplary embodiment, a surgical access device is provided and can include an elongate flexible member having proximal and distal ends and a sidewall extending therebetween and defining a longitudinal opening extending through the elongate flexible member for providing a pathway through tissue into a body cavity. The elongate flexible member can be movable between a first position in which the elongate flexible member has at least one longitudinal fold formed in the sidewall such that a width of the longitudinal opening is reduced, and a second position in which the fold in the sidewall is unfolded such that a width of the longitudinal opening is increased. In some embodiments, the elongate flexible member can be biased to each of the first and second positions.

In other embodiments, the proximal and distal ends can each have a semi-rigid ring therein. The semi-rigid ring can have at least one joint configured to allow the sidewall to fold at the longitudinal fold. The surgical access device can also include a connector matable to the proximal end of the elongate flexible member. The connector can have a seal housing removably disposed therein and can have at least one seal disposed therein and configured to seal the longitudinal opening of the elongate flexible member.

The longitudinal fold can have many configurations and in one embodiment, the longitudinal fold can include four longitudinal folds formed in the sidewall. In addition, the longitudinal fold can extend through the proximal and distal ends of the elongate flexible member. In some embodiments, the proximal and distal ends can be flared.

In other aspects, methods are provided and can include a method for accessing a body cavity. The method can include inserting an elongate shaft of an obturator through tissue and into a body cavity to create a pathway through the tissue. The elongate shaft can have a retractor disposed therearound. The method can also include radially expanding the elongate shaft in a first direction to unfold the retractor in the first direction, radially expanding the elongate shaft in a second direction different from the first direction to unfold the retractor in the second direction, and withdrawing the elongate shaft from the retractor such that the retractor forms a pathway through the tissue that provides access to the body cavity.

In some embodiments, the method can include, between the radially expanding steps, rotating the elongate shaft relative to the retractor by an angle greater than 0 degrees and less than 360 degrees, for example, by a 90 degree angle. In addition, between the radially expanding steps, the elongate shaft can be retracted. Furthermore, radially expanding the elongate shaft can include depressing an actuator on the obturator to extend a push rod and cam open extension members on the elongate shaft.

In one embodiment, a connector can be mated to a proximal end of the retractor and a seal housing can be positioned in the connector to seal the pathway formed by the retractor. In addition, the retractor can have proximal and distal flared ends that engage a tissue wall therebetween.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
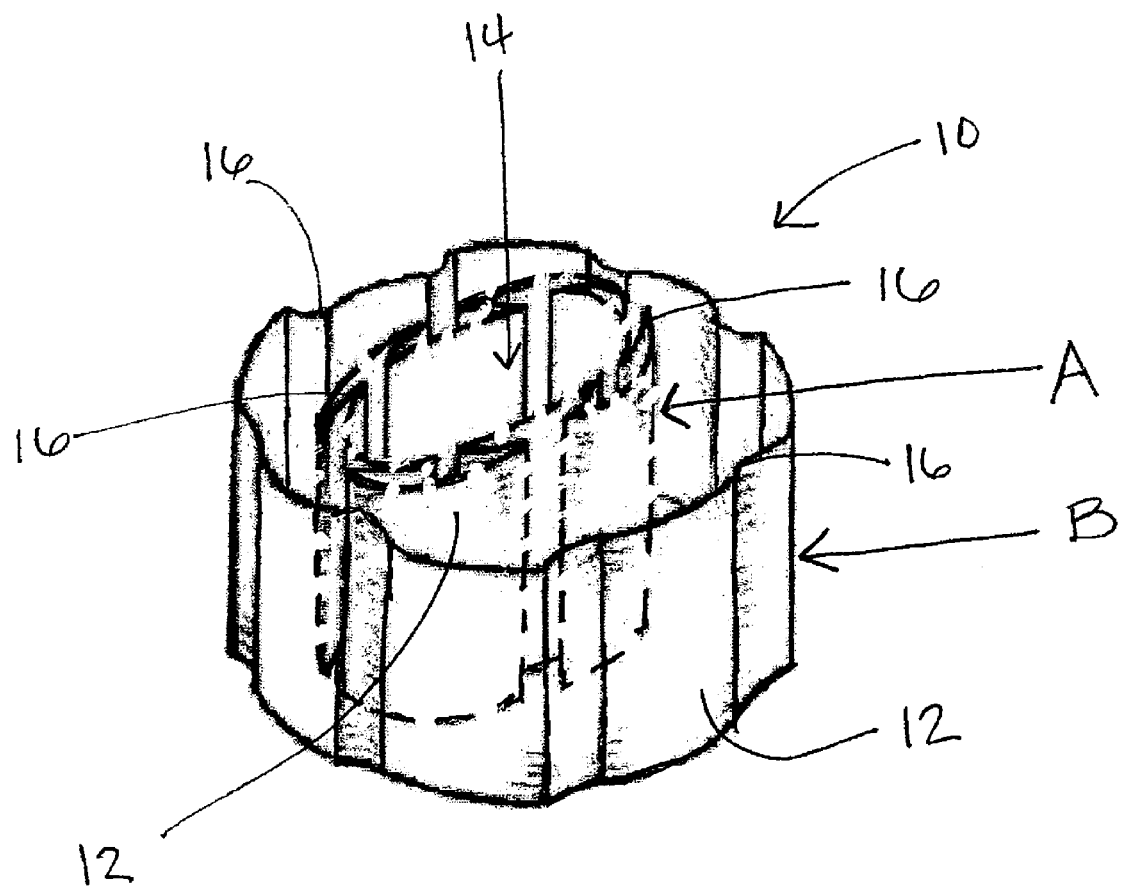
FIG. 1 is a perspective view of one embodiment of a retractor in a folded configuration and an unfolded configuration.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides improved methods and devices for providing access into a body cavity, particularly through small incisions and/or small openings in body tissue. In certain exemplary embodiments, a surgical access device is provided and can include an elongate flexible member having proximal and distal ends and a sidewall extending therebetween. The elongate flexible member can define a longitudinal opening extending therethrough for providing a pathway through tissue into a body cavity. In an exemplary embodiment, the elongate flexible member is movable between a first position in which it has one or more longitudinal folds formed in the sidewall such that a width of the longitudinal opening is reduced, and a second position in which the one or more longitudinal folds in the sidewall are unfolded such that a width of the longitudinal opening is increased. In this way, the elongate flexible member can be inserted into an incision and/or opening within tissue in a reduced dimension configuration and then expanded to a working configuration to expand the incision and/or opening. Insertion of the elongate flexible member in such a way can cause less trauma to surrounding tissue. In certain embodiments, the elongate flexible member can be biased to one or each of the first and second positions so that immediate and direct movement between the two positions can occur. The present invention also provides an obturator having an elongate shaft that can create a pathway through tissue and into a body cavity. The elongate shaft can be radially expandable to expand a flexible elongate member, for example to unfold longitudinal folds of a flexible elongate member.

The flexible elongate member can have many configurations, but it is generally used for forming a pathway through tissue to provide a working channel for inserting instruments into a body cavity. In certain exemplary embodiments, the flexible elongate member can be in the form of a semi-flexible cannula, one or more flexible sealing channels, and/or a retractor. In use, the flexible elongate member can be positioned within an opening in tissue so that surgical instruments can be inserted from outside the body to an interior body cavity. The elasticity of the skin of the patient can assist in the retention of the flexible elongate member in the body opening or incision made in the body. The flexible elongate member can be placed in any opening within a patient's body, whether a natural orifice or an opening made by an incision. For example, the flexible elongate member can be placed through the umbilicus, endoscopically including, vaginally, percutaneously, etc. The flexible elongate member can be formed of any suitable material known in the art, for example silicone, urethane, thermoplastic elastomer, and rubber.

In one exemplary embodiment illustrated in FIG. 1, a flexible elongate member in the form of a retractor 10 is provided. The retractor 10 can be formed of a flexible and foldable sidewall 12 having a tubular or cylindrical shape with a lumen 14 extending therethrough. As shown, the sidewall 12 can have one or more longitudinal pleats or folds 16 formed therein that can extend along a full longitudinal length of the sidewall 12. In other embodiments, the longitudinal folds 16 can simply extend along a portion of the length of the sidewall 12. As will be appreciated by those skilled in the art, any type of fold 16 can be used, including, but not limited to, single bends or creases, multiple bends or creases, tri-folds, accordion folds, knife pleats, fluted pleats, star folds, etc. In addition, the longitudinal folds 16 can be positioned anywhere on the sidewall 12 of the retractor 10 and at any distance apart from each other around the sidewall 12. The folds also need not include creases or bends, but can be in the form of rolled and/or wrapped portions.

The longitudinal folds 16 can allow a size of the lumen 14 extending through the retractor 10 to be decreased, for example, when the longitudinal folds 16 are folded. In addition, the longitudinal folds 16 can allow a size of the lumen 14 extending through the retractor 10 to be increased, for example, when the longitudinal folds 16 are unfolded. The ability to decrease and increase a size of the lumen 14 of the retractor 10 as needed, and thus a size of the retractor 10, allows the retractor 10 to be more easily positioned within particularly small incisions and/or openings. In turn, this can reduce trauma to the surrounding tissue when a smaller incision or opening is used.

While the retractor 10 can have various configurations, the retractor 10 is shown in FIG. 1 in two of its possible configurations. In a folded configuration A, the longitudinal folds 16 are folded such that a size of the lumen 14 of the retractor 10 is decreased when compared with the unfolded configuration B. In configuration B, the longitudinal folds 16 are unfolded such that the size of the lumen 14 is increased. As will be appreciated by those skilled in the art, in some situations, all of the folds 16 can be either folded or unfolded. In other situations, one or more of the longitudinal folds 16 can be unfolded while one or more other longitudinal folds 16 can remain folded.

Figure 2:
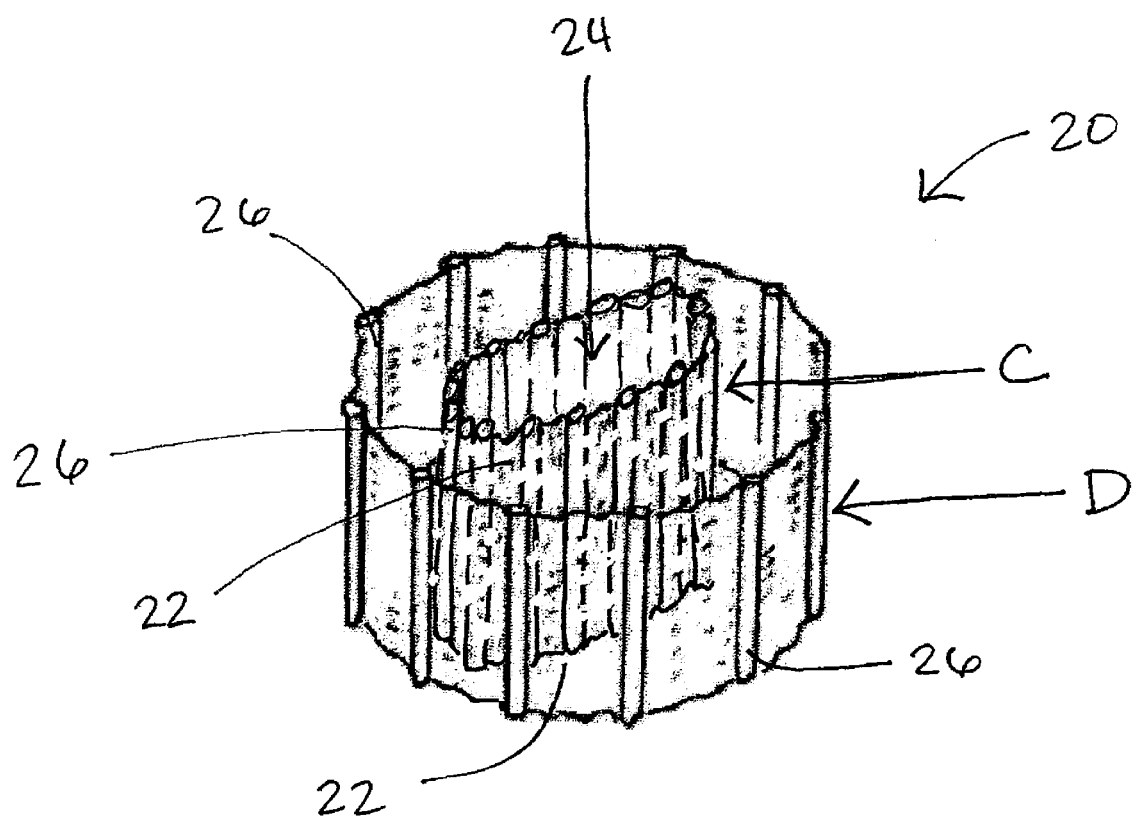
FIG. 2 is a perspective view of another embodiment of a retractor in a folded configuration and an unfolded configuration.

Another embodiment of a foldable retractor 20 having a lumen 24 extending therethrough is illustrated in FIG. 2. In this embodiment, multiple reinforcing ridges or ribs 26 are included within the sidewall 22 such that, in a folded configuration, the sidewall 22 folds and bunches longitudinally between the ribs 26. In an unfolded configuration shown in FIG. 2A, the portion of sidewall 22 between the ribs 26 unfolds and expands such that there is a greater distance between each of the ribs 26. More particularly, in a folded configuration C, the ribs 26 are closer together and the sidewall 22 is longitudinally folded to decrease a size of the lumen 24. In an unfolded configuration D, the ribs 26 are spaced further apart and the sidewall 22 is unfolded to increase the size of the lumen 24. As will be appreciated by those skilled in the art, the ribs 26 can be formed integrally with the retractor 20 and/or can be positioned within fluted longitudinal openings formed in the sidewall 22 of the retractor 20.

Figure 3A:
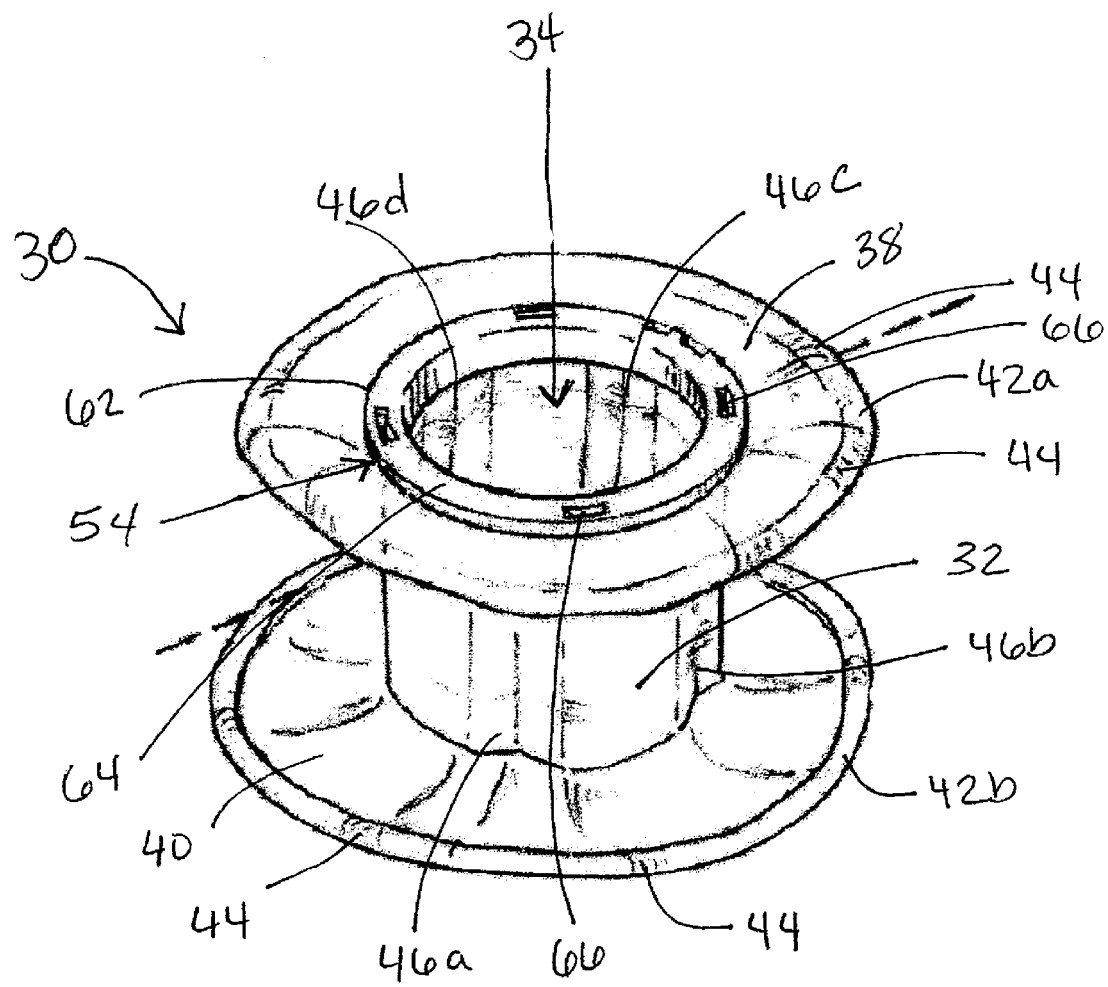
FIG. 3A is a perspective view of still a further embodiment of an unfolded retractor with flared proximal and distal ends.
Figure 3B:
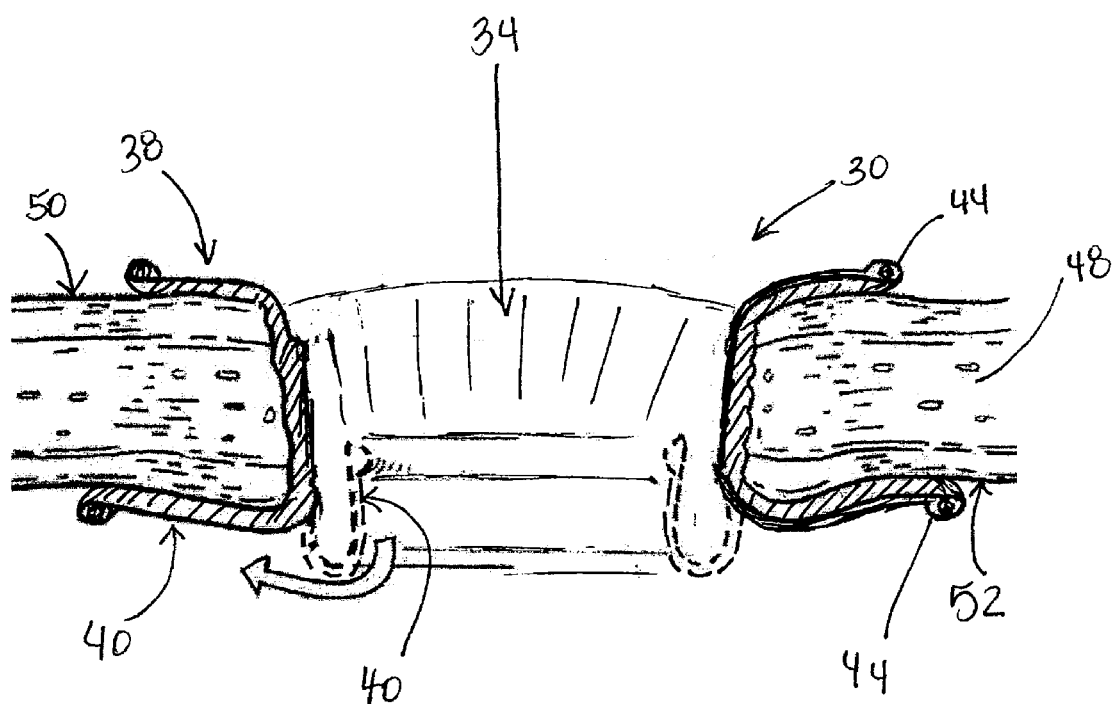
FIG. 3B is a cross-sectional view of the retractor of FIG. 3A positioned within tissue.
Figure 3C:
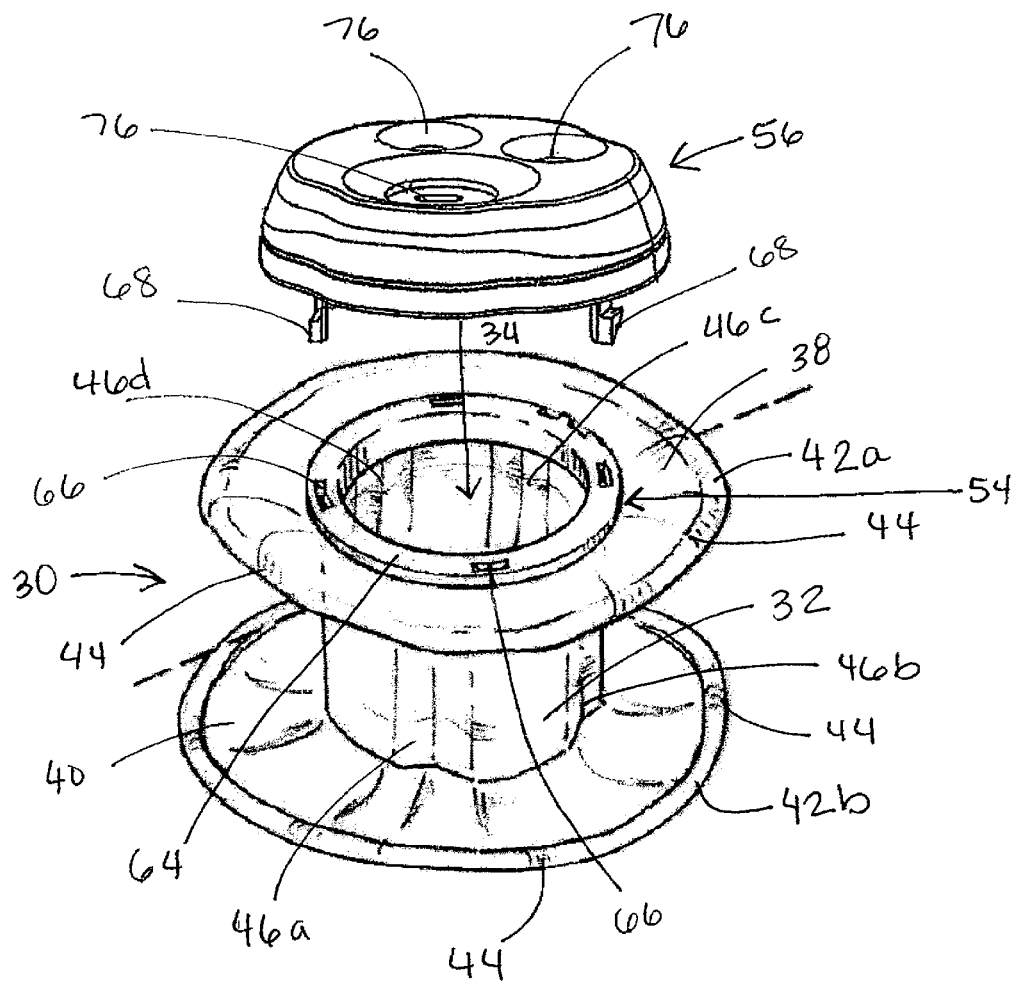
FIG. 3C is a perspective view of the retractor of FIG. 3A and a seal assembly attachable to the retractor.

The retractors described herein can have many other configurations. For example, another exemplary retractor 30 is illustrated in FIGS. 3A-3C. In this embodiment, the retractor 30 has flared proximal and distal ends 38, 40 with a sidewall 32 extending longitudinally therebetween. The proximal and distal ends 38, 40 can each have an opening formed therethrough defining open ends of a working channel or lumen 34 that is defined by the sidewall 32. The proximal and distal ends 38, 40 can also each have an o-ring 42a, 42b formed around an outer circumference thereof to aid in providing rigidity and/or structure to the flared ends 38, 40. In some embodiments, the o-rings 42a, 42b are integrally formed with the flared proximal and distal ends 38, 40. In other embodiments, the o-rings 42a, 42b can be separate components that are positioned within openings extending around the outer circumference of the proximal and distal ends 38, 40. In general, an outer diameter of the proximal and distal ends 38, 40 is greater than an inner diameter of the lumen 24 so that the ends 38, 40 rest against and engage tissue therebetween.

As shown, the retractor 30 can also have one or more longitudinal folds formed therein, similar to those described above with respect to FIGS. 1 and 2. In this particular embodiment, the retractor 30 has four longitudinal folds 46a, 46b, 46c, 46d that extend through the proximal and distal ends 38, 40 so that the proximal and distal ends 38, 40 can also be folded. The longitudinal folds 46a, 46b, 46c, 46d are positioned such that folds 46a and 46c are opposite one another, and folds 46b and 46d are opposite to one another. The o-rings 42a, 42b positioned around the outer circumference of the proximal and distal ends 38, 40 can also have one or more creases, joints, folds, and/or hinges formed therein. For example, the o-rings 38, 40 can have multiple folds 44 formed therein that allow the o-rings 38, 40 to fold and expand with the retractor 30. In this way, a size of the entire retractor 30, including a size of the lumen 34, can be decreased when folded and increased when unfolded. In other embodiments, the proximal and distal ends 38, 40 need not be folded at all and one or both can be folded into the lumen 24, as described below.

FIG. 3B illustrates the retractor 30 positioned within an incision or opening in tissue 48. As shown, the flared distal end 40 of the retractor 30 can be folded up and into the lumen 34 of the retractor 30 for delivery into the tissue 48 (as shown in phantom). In the same way, the flared proximal end 38 can be folded down and into the lumen 34 of the retractor 30 for delivery into the tissue 48. Once positioned within the tissue 48, the retractor 30 is unfolded to both expand a size of the lumen 34 and to deploy the proximal and distal ends 38, 40. Once fully expanded, as shown, the flared proximal end 38 is positioned on an external surface 50 of the tissue 48 while the flared distal end 40 is positioned on an interior surface 52 of the tissue 48. Both the flared proximal and distal ends 38, 40 provide additional stabilization for the retractor 30, as well as a seal between the tissue 48 and the retractor 30. In some embodiments, the distal end 40 can remain unfolded, whether alone or within a connector, during insertion and unfolding of the sidewall 32 and proximal end 38 of the retractor 30.

In any and all of the elongate flexible member embodiments described herein, any suitable material and mechanism can be used to provide folds therein. For example, the elongate flexible member and/or a fold or joint in the elongate flexible member can be formed of or can include a shape memory material having pseudoelastic or superelastic properties. A shape memory material is generally characterized by having two distinct states and an ability to restore itself to a preselected, predetermined, or preconfigured shape of a particular state after plastic deformation. For example, the shape memory material can be a shape memory polymer or alloy, such as nitinol (a nickel-titanium alloy), to allow for a change in shape from a folded configuration to an unfolded configuration. In addition, joints, natural hinges, and other mechanical mechanisms known in the art can be used to achieve longitudinal folds in the elongate flexible member and/or folds in any o-rings positioned within the proximal and distal ends of an elongate flexible member. The materials and/or other features can also be used to bias the elongate flexible member to one or each of the folded and unfolded configurations.

As also shown in FIGS. 3A and 3C, a connector 54 can be coupled to a proximal portion 62 of the retractor 30. The connector 54 can be used to seat and receive a seal assembly 56 for sealing the lumen 34 of the retractor 30, such as that shown, for example, in FIG. 3C. The connector 54 can have any configuration, but in the illustrated embodiment, the connector 54 is a circular or o-shaped component having an opening extending therethrough that corresponds to the opening through the retractor 30. A superior surface 64 of the connector 54 can include slots 66 to receive latches 68 of the seal assembly 56. The connector 54 can mate to the retractor 30 by any mating mechanism known in the art, threadable engaging an interior wall of the retractor.

In other embodiments, a bayonet connector can be used to couple a retractor to a seal assembly. The bayonet connector can hold and enclose a proximal end of the retractor, such as that shown in FIGS. 5-9, and can mate to the seal assembly through a bayonet connection, for example, such as that described in U.S. application Ser. No. 12/399,625 filed on Mar. 6, 2009 and entitled "Methods and Devices for Providing Access into a Body Cavity," which is hereby incorporated by reference in its entirety.

Once the retractor 30 and the connector 54 are positioned within the tissue 48, a seal assembly 56 can be latched or otherwise attached to connector 54. Once attached, the seal assembly 56 can seal the lumen 34 of the retractor 30 using one or more sealing elements 76 formed or positioned therein for receiving surgical instruments therethrough. Details of exemplary seal assemblies that can be used with the retractors described herein can be found, for example, in U.S. application Ser. No. 12/242,765 entitled "Surgical Access Device," filed on Sep. 30, 2008; U.S. application Ser. No. 12/242,721 entitled "Multiple Port Surgical Access Device," filed on Sep. 20, 2008; and U.S. application Ser. No. 12/399,547 entitled "Surgical Access Devices and Method Providing Seal Movement in Predefined Paths," all of which are incorporated herein by reference in their entireties.

The present invention also provides an obturator for inserting the retractors described herein, or any retractor or other access device known in the art, into an incision and/or opening within tissue. For example, in FIGS. 4A-4D, an obturator 100 is provided for inserting a retractor 108 into an incision and deploying it therein. As shown, the obturator 100 generally includes an actuator 102 and an obturator shaft 104 having two expansion members 106a, 106b. The illustrated obturator shaft 104 is a cylindrical, elongate member with a blunt tip 110 at a distal-most end. One or more blades or wings 112 can be formed on the blunt tip 110 to assist in moving the obturator 100 through tissue with minimal damage to the tissue. In some embodiments, the wings 112 can be positioned approximately 180 degrees apart.

Figure 4A:
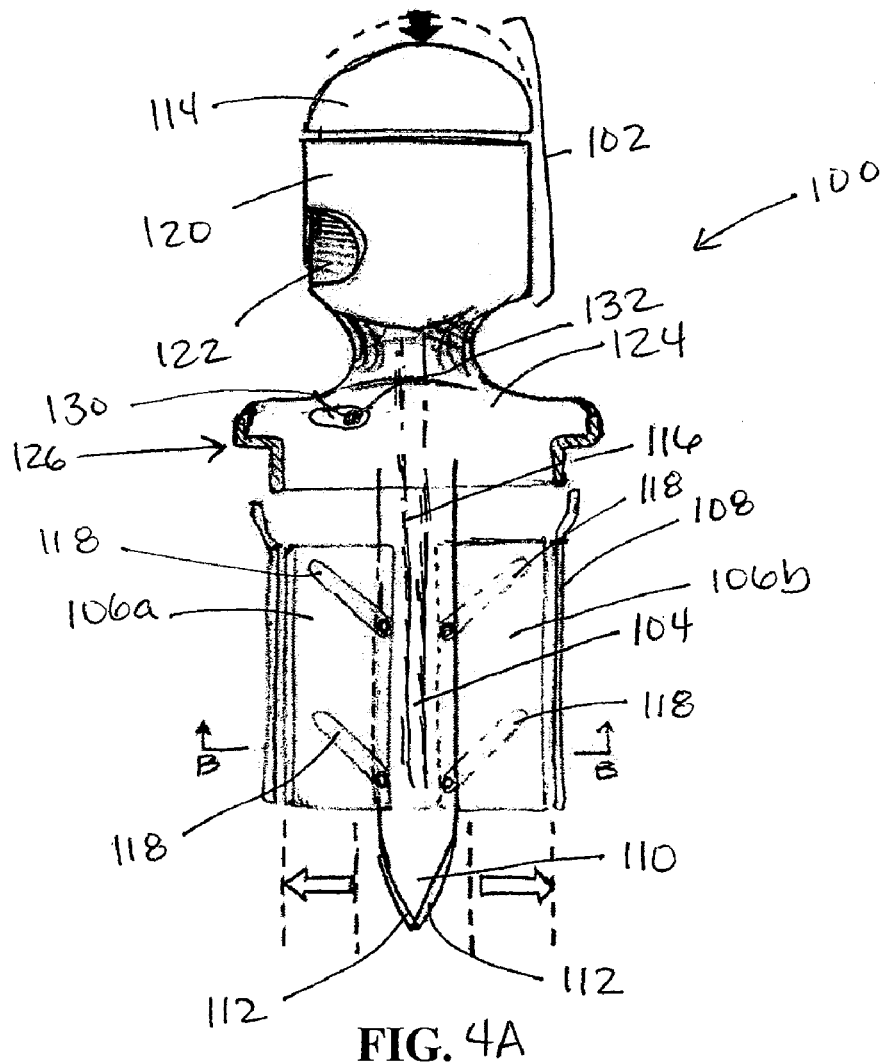
FIG. 4A is a cross-sectional view of one embodiment of an obturator used for expanding an exemplary retractor.
Figure 4B:
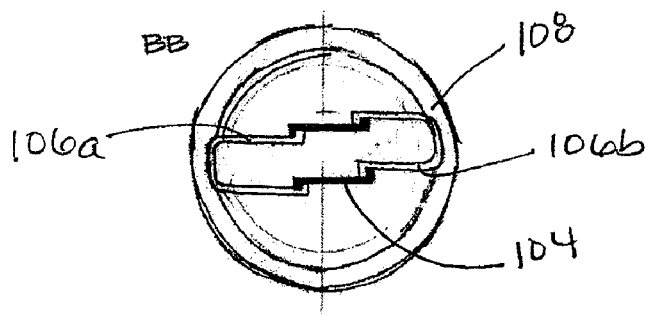
FIG. 4B is a longitudinal cross-sectional view of the obturator of FIG. 4A in a retracted configuration.
Figure 4C:
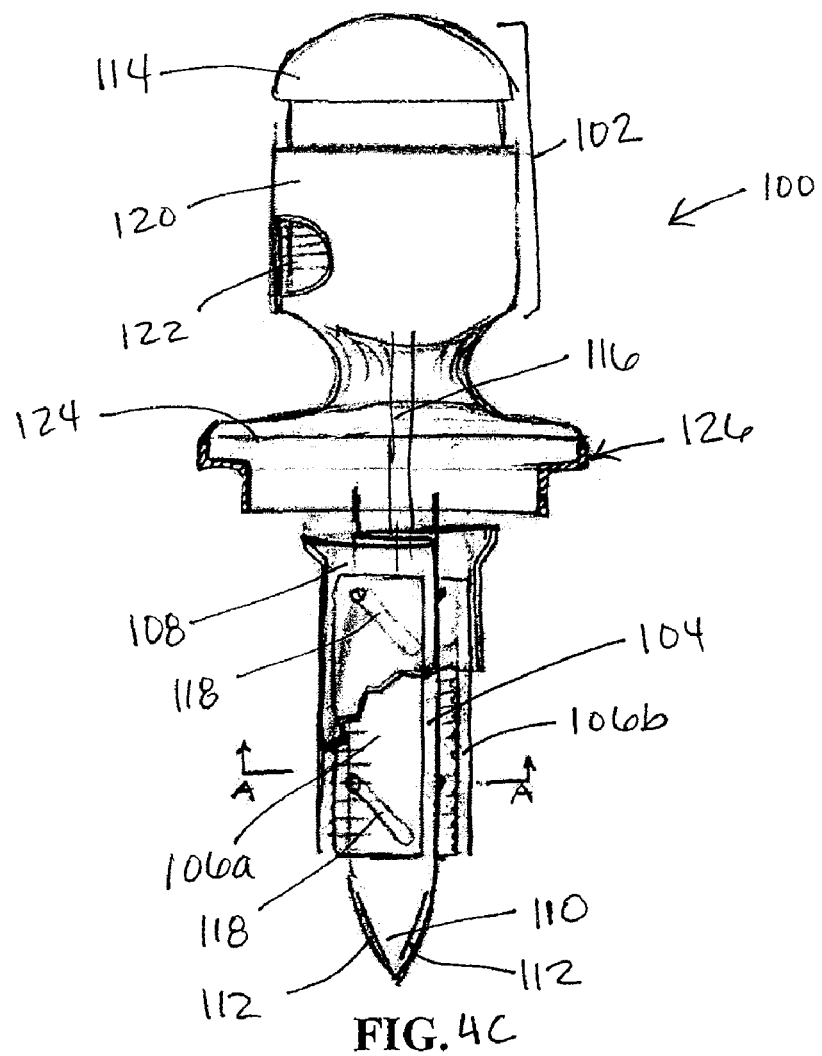
FIG. 4C is another cross-sectional view of the obturator of FIG. 4A.
Figure 4D:
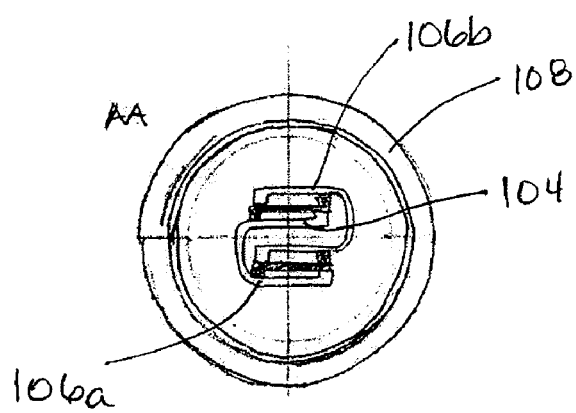
FIG. 4D is another longitudinal cross-sectional view of the obturator of FIG. 4A in an expanded configuration.

The expansion members 106a, 106b can generally be used to unfold and expand the retractor 108 by pressing against the retractor folds and causing them to unfold. They can be attached to opposed sides of the obturator shaft 104 and thus can have any shape and configuration. In some embodiments, as shown in FIGS. 4B and 4D, they can be generally u-shaped such that a cross-sectional shape of the obturator shaft 104, when the expansion members 106a, 106b are extended, is substantially oblong. In other embodiments, the expansion members 106a, 106b can be in the form of opposed jaws that open as they expand away from the obturator shaft 104 and close as they are retracted back to the shaft 104. The retractor 108 can generally be positioned around the expansion members 106a, 106b and the obturator shaft 104 in an initial folded configuration. The actuator 102 can facilitate the extension of the expansion members 106a, 106b to thereby expand the retractor to an unfolded configuration once in place within tissue.

In some embodiments, the obturator 100 can move from a first position in which the retractor lumen has a reduced width less than its maximum width or a maximum width, and a second position in which the retractor can have a maximum width or a width less than its maximum width. In either position, a cross-sectional shape of the expansion members and/or of the retractor lumen can be circular, oblong, ovular, etc.

The actuator 102 can communicate with the expansion members 106a, 106b through any mechanism, whether mechanical or electrical, known in the art. In the illustrated embodiment, the actuator 102 includes an actuator lever 114 that is coupled to a push rod 116. The push rod 116 is attached to proximal and distal linkages 118 which are, in turn, coupled to the expansion members 106a, 106b. When the actuator lever 114 is depressed into an actuator base 120, the push rod 116 moves distally causing the proximal and distal linkages 118 to cam the expansion members 106a, 106b outward away from the obturator shaft 104. This movement is capable of unfolding the retractor 108, as will be described in more detail below. An actuator release 122 can be pressed to release the actuator lever 114 and return the expansion members 106a, 106b to their retracted state, or alternatively, the actuator lever 114 can be pulled proximally.

In other embodiments, an actuator can be in the form of pliers handles or a trigger assembly that allows expansion members and/or jaw members to be extended individually. For example, the actuator can have two finger loops or handles that are pivotally connected to one another and are each connected to one of the expansion members. In this way, one of the handles can be moved to extend or retract one of the expansion member independently from the other. A person skilled in the art will appreciate the variety of mechanisms that can be used to extend and retract the expansion members.

In another embodiment, the obturator 100 can also have a housing 124 that is formed adjacent to the actuator base 120 and that is able to seat a retractor connector (not shown) and release it once the retractor 108 is in place. The connector can couple to a base 126 of the obturator housing 124. A connector release 130 can be included in the housing 124. The release 130 can slide within its slot 132 to cause a latch mechanism to release the connector once it is in place within the retractor 108.

In use, as shown in FIGS. 5-9, before inserting the obturator 100, a small incision can be made through tissue 134. In other embodiments, a natural opening in the body can be used. The retractor 108 can be initially in a folded configuration and positioned around the obturator shaft 104 with the expansion members 106a, 106b fully expanded. The blunt tip 110 of the obturator 100 can be inserted into the incision and/or opening and can be gently maneuvered through the tissue 134 to slowly form a pathway through the tissue and into the body cavity. The wings 112 on the tip 110 can assist in pushing aside muscle fibers and the various layers of tissue so that minimal cutting of tissue is needed.

Figure 5:
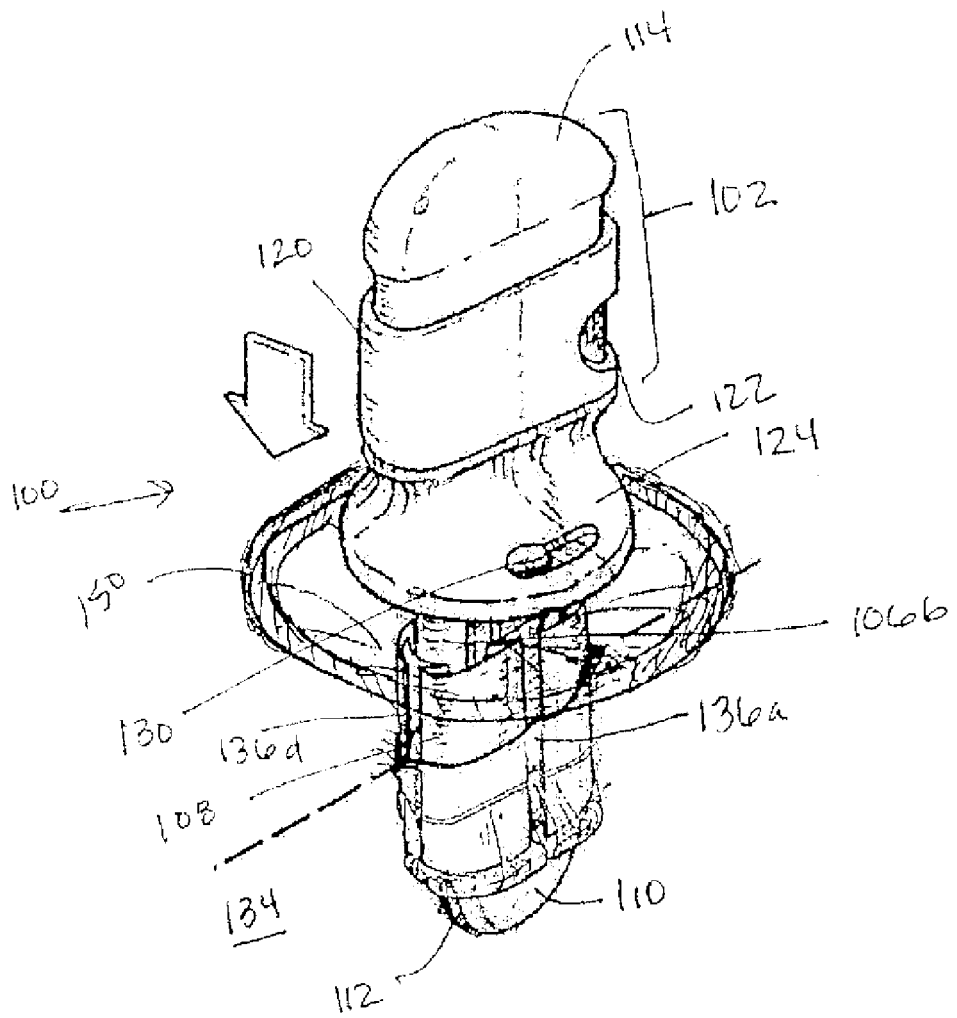
FIG. 5 is a perspective view of the obturator of FIGS. 4A and 4C having the retractor disposed therearound and being inserted into tissue.
Figure 6:
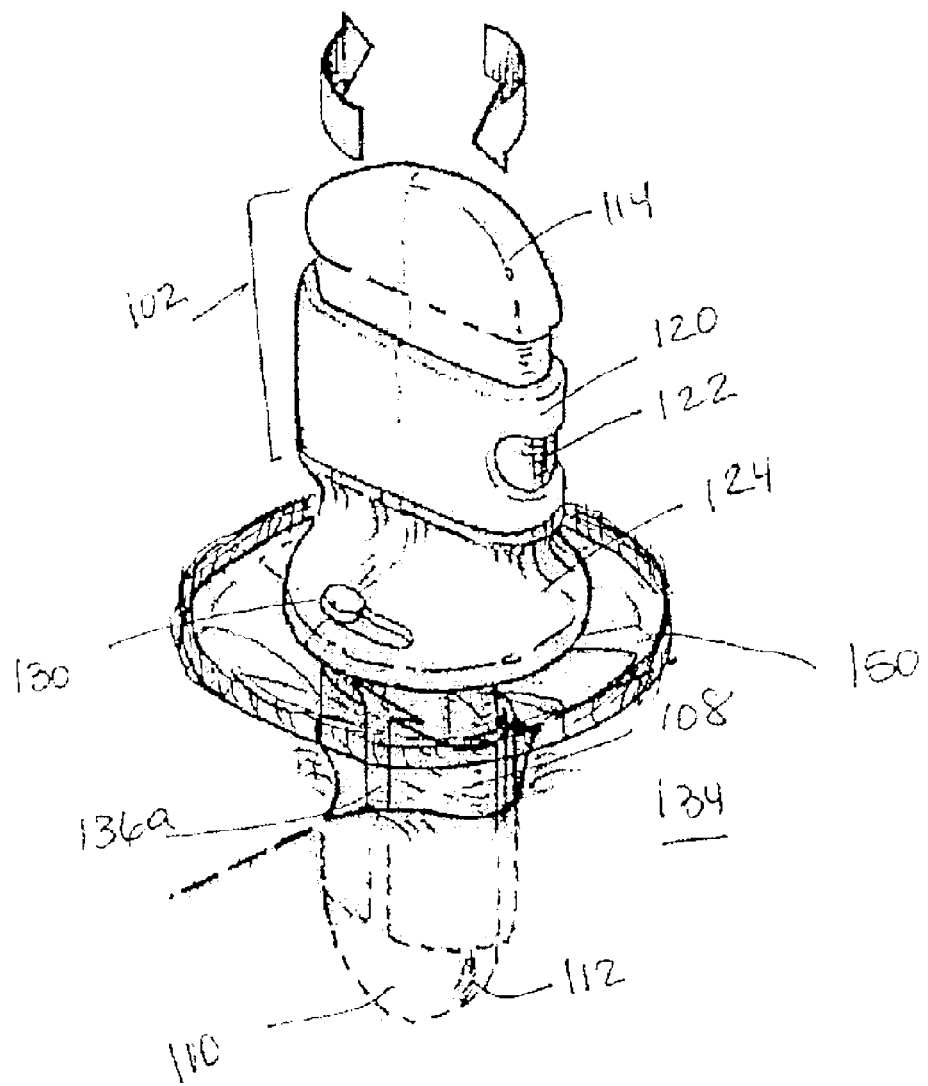
FIG. 6 is a perspective view of the obturator and the retractor of FIG. 5 illustrating the retractor being rotated within the tissue.
Figure 7:
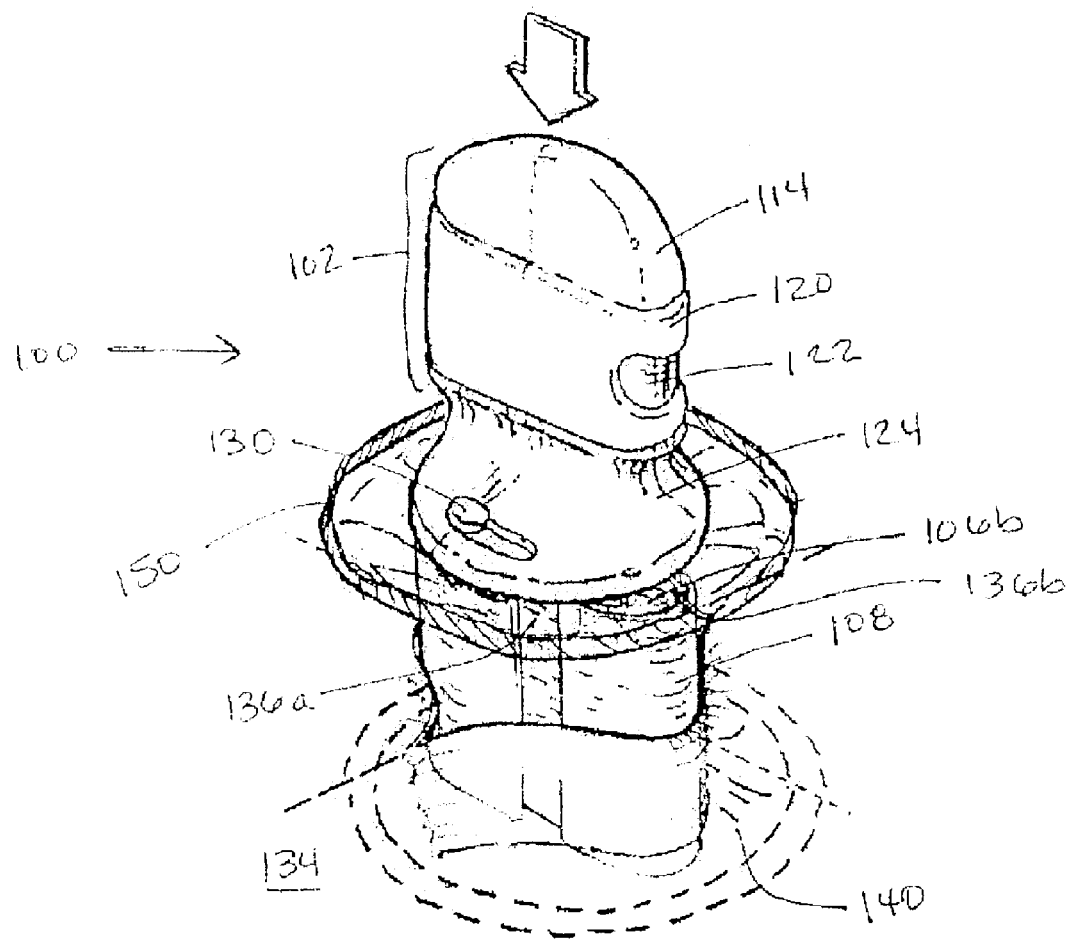
FIG. 7 is a perspective view of the obturator and the retractor of FIG. 6 illustrating the obturator expanded in a first direction to expand the retractor in a first direction.
Figure 8:
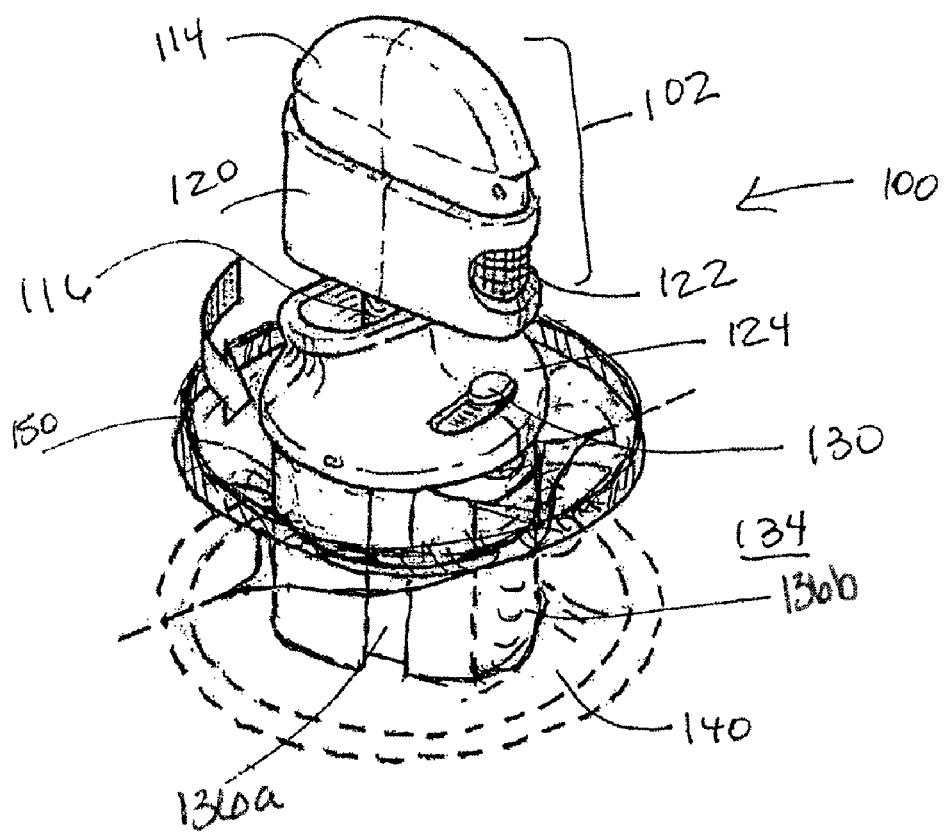
FIG. 8 is a perspective view of the obturator and the retractor of FIG. 7 illustrating the obturator rotated to expand the retractor in a second direction.

Once the obturator 100 and the retractor 108 are positioned to an appropriate depth within the tissue as shown in FIG. 5, the obturator 100 can optionally be turned by some angle, for example by 90 degrees, to enlarge the incision, as indicated by the arrow in FIG. 6. In addition, in an embodiment in which the expansion members 106a, 106b are independently movable, one of the expansion members 106a, 106b can be extended and the obturator 100 rotated to enlarge the incision. In other embodiments, the retractor 108 can be unfolded immediately, without rotation of the obturator 100. In either embodiment, once the obturator 100 is in place, the retractor 108 can be unfolded by the expansion members 106a, 106b. The actuator lever 114 can be depressed into the actuator base 120 to cam the expansion members 106a, 106b outward in a first direction, as shown in FIG. 7. The expansion members 106a, 106b will push against two of the opposed folds 136b, 136d, causing the retractor 108 to unfold in that direction, as shown in FIG. 7. Because the longitudinal folds 136a, 136b, 136d (a fourth fold is obscured in FIGS. 5-9) are biased to a folded configuration and an unfolded configuration, the two opposed folds 136b, 136d will move directly from the folded configuration to an unfolded configuration in response to extension of the expansion members 106a, 106b. In addition, the distal end 140 can unfold from the interior of the retractor 108.

Figure 9:
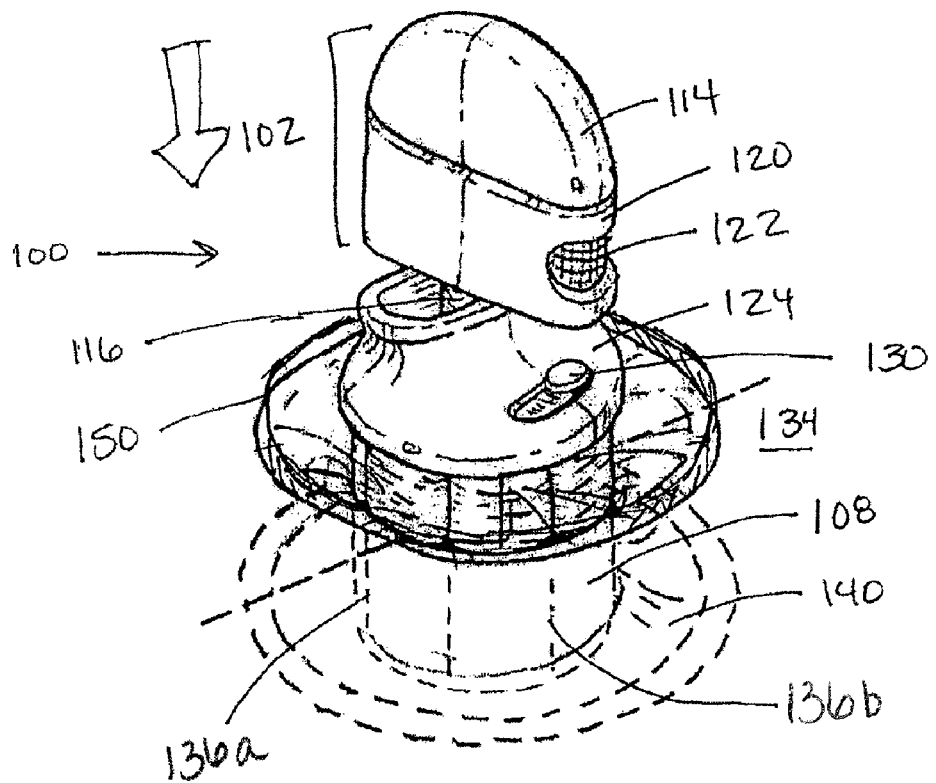
FIG. 9 is a perspective view of the obturator and the retractor of FIG. 8 illustrating the retractor fully expanded.

In some embodiments, the actuator release 114 can be pressed to release the expansion members 106a, 106b and cause them to retract to the obturator shaft 104. The obturator 110 can then be rotated within the retractor 108, for example by 90 degrees, as shown in FIG. 8, and expanded again in a second direction to cause the remaining two opposed longitudinal folds 136a (the other fold is obscured as mentioned above) to unfold, resulting in a fully deployed retractor 108 within the tissue, as shown in FIG. 9. The connector release 130 can then be actuated to cause a connector 150 to release from the obturator housing 124. The connector 150 remains attached to the retractor 108 ready to receive a seal assembly, as described above.

In other embodiments, once the expansion members 106a, 106b have been extended in a first direction, the expansion members 106a, 106b can remain extended. The obturator 100 can then be rotated within the retractor 108 about its longitudinal axis by an amount effective to sweep open the other longitudinal folds 136a, (the other fold is obscured, as mentioned above) in the retractor 108 to thereby fully expand the retractor 108. Once the retractor 108 is fully open, the expansion members 106a, 106b can be retracted and the connector 150 attached as described above. As will be appreciated by those skilled in the art, one fold to any number of folds in a retractor 108 can be unfolded using the above noted techniques. A seal assembly can be attached to the connector 150 to provide sealed surgical access into the body cavity. One or more surgical instruments can be inserted through the seal assembly, including through one or more seals within the seal assembly, through the lumen of the retractor 108, and into the body cavity to perform surgical procedures.

As will also be appreciated by those skilled in the art, any and all of the elongate flexible member, obturator, and seal assembly embodiments disclosed herein can be interchangeable with one another as needed. For example, a kit could include multiple elongate flexible members, obturators, and seal assemblies.

As surgical instruments are inserted through the elongate flexible member embodiments described herein, a risk can exist that a particularly sharp instrument may tear or puncture a portion of the elongate flexible member. Accordingly, in any and all of the embodiments described herein, a safety shield can optionally be included to reduce the risk of tearing or puncture by a surgical instrument. The safety shield can include one or more longitudinal folds comparable to that of the elongate flexible member to allow for ease of insertion as described above. In general the shield can be of a material that is relatively smooth to allow ease of passage of instruments, but resistant to tearing and puncture. For example, the shield can be formed of silicone, urethane, thermoplastic elastomer, rubber, polyolefins, polyesters, nylons, fluoropolymers, and any other suitable materials known in the art.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
an obturator having an elongate shaft configured to create a pathway through tissue and into a body cavity, the elongate shaft being radially expandable; and
a flexible retractor having a longitudinal opening extending therethrough and configured to form a pathway through tissue for providing access to a body cavity, the flexible retractor including first and second longitudinal folds formed therein and configured such that insertion of the elongate shaft of the obturator into the opening in a first position and radial expansion of the elongate shaft unfolds the first longitudinal fold, and repositioning the elongate shaft to a second position, different than the first position within the opening unfolds the second longitudinal fold to radially expand the longitudinal opening and thereby increase a size of a pathway formed through tissue when the flexible retractor is disposed within tissue.

2. The surgical access device of claim 1, wherein the obturator includes an actuator effective to expand and retract the elongate shaft.

3. The surgical access device of claim 1, wherein the flexible retractor includes third and fourth longitudinal folds formed therein, wherein the first fold and the third fold are opposed and the second fold and the fourth fold are opposed.

4. The surgical access device of claim 3, wherein the elongate shaft is configured to expand in a first direction to unfold the first and third longitudinal folds when the elongate shaft is in the first position, and the elongate shaft is configured to expand in a second direction to unfold the second and fourth longitudinal folds when t is in the seco position.

5. The surgical access device of claim 4, wherein the first direction and the second direction are offset by approximately 90 degrees.

6. The surgical access device of claim 1, wherein the first and second longitudinal folds are biased to a folded state and to an unfolded state.

7. The surgical access device of claim 1, wherein the cross-sectional shape of the elongate shaft is oblong in an expanded configuration.

8. The surgical access device of claim 1, wherein the elongate shaft has first and second expansion members coupled thereto, and radial expansion of the elongate shaft includes moving the first and second expansion members from an unexpanded configuration to an expanded configuration, wherein a longitudinal axis of each of the first and second expansion members are substantially parallel to a longitudinal axis of the elongate shaft both in the unexpanded configuration and in the expanded configuration.

9. The surgical access device of claim 8, wherein each of the first and second expansion members can be independently expanded without expanding the other of the first and second expansion members.

10. The surgical access device of claim 8, wherein the first and second expansion members are coupled to the elongate shaft by first and second linkages.

11. The surgical access device of claim 1, wherein the elongate shaft is configured to be rotated within the longitudinal opening when the elongate shaft extends through the longitudinal opening, the elongate shaft being in a first rotated position to unfold the first longitudinal fold and in a second rotated position, different from the first rotated position to unfold the second longitudinal fold.

12. The surgical access device of claim 1, wherein after unfolding the first longitudinal fold, the elongate shaft is configured to be radially contracted, and after the elongate shaft is repositioned to the second position, the elongate shaft is configured to be radially expanded to unfold the second longitudinal fold.

13. The surgical access device of claim 1, wherein the obturator is configured to expand the flexible retractor asymmetrically when the obturator unfolds the first longitudinal fold.

14. The surgical access device of claim 1, wherein the second longitudinal fold remains in a folded configuration when the first longitudinal fold is unfolded.

15. A surgical access device, comprising:
an elongate flexible member having proximal and distal ends and a sidewall extending therebetween and defining a longitudinal opening extending through the elongate flexible member for providing a pathway through tissue into a body cavity, the elongate flexible member being movable between a first position in which the elongate flexible member has first and second longitudinal folds formed in the sidewall and a second position in which the second longitudinal fold remains folded and the first longitudinal fold in the sidewall is unfolded such that a width of the longitudinal opening is increased from a width of the longitudinal opening in the first position, and wherein the elongate flexible member is biased to each of the first and second positions, and wherein the distal end has a semi-rigid ring therein, the semi-rigid ring having at least one fold formed therein that is configured to allow the semi-rigid ring to fold at the at least one fold.

16. The surgical access device of claim 15, further comprising a connector mated to the proximal end of the elongate flexible member, the connector having a seal housing removably disposed therein and having at least one seal disposed therein and configured to seal the longitudinal opening of the elongate flexible member.

17. The surgical access device of claim 15, wherein the elongate flexible member has two additional longitudinal folds formed in the sidewall.

18. The surgical access device of claim 15, wherein the first and second longitudinal folds extends through the distal end of the elongate flexible member.

19. The surgical access device of claim 15, wherein the proximal and distal ends are flared with respect to the sidewall.

* * * * *